United States Patent
Lundberg

(10) Patent No.: US 8,834,372 B2
(45) Date of Patent: Sep. 16, 2014

(54) SYSTEM AND METHOD FOR OPTIMIZED SPATIO-TEMPORAL SAMPLING

(75) Inventor: Andrew K. Lundberg, Woodinville, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 853 days.

(21) Appl. No.: 11/749,319

(22) Filed: May 16, 2007

(65) Prior Publication Data

US 2008/0183079 A1    Jul. 31, 2008

Related U.S. Application Data

(60) Provisional application No. 60/886,877, filed on Jan. 26, 2007.

(51) Int. Cl.
*A61N 5/00* (2006.01)
*G01S 15/89* (2006.01)
*A61B 8/08* (2006.01)

(52) U.S. Cl.
CPC .............. *G01S 15/8993* (2013.01); *A61B 8/08* (2013.01)
USPC ....................................... 600/443

(58) Field of Classification Search
CPC ............................. G01S 15/8993; A61B 8/08
USPC ....................................... 600/443
See application file for complete search history.

(56) References Cited

U.S. PATENT DOCUMENTS

| | | | |
|---|---|---|---|
| 4,649,927 A * | 3/1987 | Fehr et al. ................... | 600/443 |
| 4,653,505 A * | 3/1987 | Iinuma ........................ | 600/437 |
| 5,603,318 A | 2/1997 | Heilbrun et al. | |
| 5,913,824 A | 6/1999 | Ogasawara et al. | |
| 6,048,312 A | 4/2000 | Ishrak et al. | |
| 6,123,670 A | 9/2000 | Mo | |
| 6,216,029 B1 | 4/2001 | Pailtieli | |
| 6,233,476 B1 | 5/2001 | Strommer et al. | |
| 6,317,621 B1 | 11/2001 | Graumann et al. | |
| 6,390,981 B1 | 5/2002 | Jago | |

(Continued)

FOREIGN PATENT DOCUMENTS

| | | |
|---|---|---|
| CN | 101231457 | 7/2008 |
| CN | 101231457 A | 7/2008 |
| EP | 1950582 | 7/2008 |
| WO | WO-2006/089426 | 8/2006 |

OTHER PUBLICATIONS

International Search Report issued for PCT/US2008/075367 dated Nov. 14, 2008, 9 pgs.

(Continued)

*Primary Examiner* — Tse Chen
*Assistant Examiner* — Hien Nguyen
(74) *Attorney, Agent, or Firm* — Perkins Coie LLP

(57) ABSTRACT

The present invention is directed to a system and method for spatial compounding on an ultrasound platform to achieve optimized spatio-temporal sampling. This is accomplished by a system and method for mixing the order of steered and straight rays fired within a frame. In one embodiment this is accomplished by changing the firing sequence so that the target region is sampled in subsequent lines as opposed to subsequent frames. Using this approach it is possible to minimize the temporal image artifacts caused by the compounding process. This effectively changes the ray firing sequence to move the location of minimal temporal difference to the desired target point.

2 Claims, 4 Drawing Sheets

(56) References Cited

U.S. PATENT DOCUMENTS

| | | |
|---|---|---|
| 6,390,982 B1 | 5/2002 | Bova et al. |
| 6,405,072 B1 | 6/2002 | Cosman |
| 6,423,004 B1 | 7/2002 | Dong et al. |
| 6,490,477 B1 | 12/2002 | Zylka et al. |
| 6,511,426 B1 | 1/2003 | Hossack et al. |
| 6,524,252 B1 | 2/2003 | Yu et al. |
| 6,591,130 B2 | 7/2003 | Shahidi |
| 6,611,141 B1 | 8/2003 | Schulz et al. |
| 6,708,055 B2 | 3/2004 | Geiser et al. |
| 6,733,458 B1 | 5/2004 | Steins et al. |
| 6,790,181 B2 | 9/2004 | Cai et al. |
| 7,386,339 B2 | 6/2008 | Strommer et al. |
| 7,601,121 B2 | 10/2009 | Pagoulatos et al. |
| 7,658,713 B2 | 2/2010 | Barnes et al. |
| 7,925,068 B2 | 4/2011 | Hoctor et al. |
| 2002/0049375 A1 | 4/2002 | Strommer et al. |
| 2002/0165448 A1 | 11/2002 | Ben-Haim et al. |
| 2003/0050557 A1 | 3/2003 | Susil et al. |
| 2003/0092989 A1* | 5/2003 | Aichhorn et al. ............. 600/443 |
| 2003/0130576 A1 | 7/2003 | Seeley et al. |
| 2003/0135119 A1* | 7/2003 | Lee et al. ...................... 600/461 |
| 2003/0220559 A1 | 11/2003 | Ehnholm et al. |
| 2004/0006266 A1 | 1/2004 | Ustuner et al. |
| 2005/0002570 A1 | 1/2005 | Clark et al. |
| 2005/0171429 A1 | 8/2005 | Mathew et al. |
| 2005/0215893 A1 | 9/2005 | Barnes et al. |
| 2005/0288588 A1 | 12/2005 | Weber et al. |
| 2006/0098853 A1 | 5/2006 | Roundhill et al. |
| 2006/0241432 A1 | 10/2006 | Herline et al. |
| 2007/0016039 A1 | 1/2007 | Vortman et al. |
| 2007/0055126 A1 | 3/2007 | Yu et al. |
| 2007/0073136 A1 | 3/2007 | Metzger |
| 2007/0100234 A1 | 5/2007 | Arenson et al. |
| 2007/0167806 A1 | 7/2007 | Wood et al. |
| 2007/0193354 A1 | 8/2007 | Felix et al. |
| 2007/0239020 A1* | 10/2007 | Iinuma et al. ................. 600/459 |
| 2008/0021300 A1 | 1/2008 | Allison |
| 2008/0114255 A1 | 5/2008 | Schwartz et al. |
| 2008/0119735 A1* | 5/2008 | Lin et al. ....................... 600/450 |
| 2008/0183079 A1 | 7/2008 | Lundberg et al. |
| 2008/0188752 A1 | 8/2008 | Randall et al. |
| 2008/0221425 A1 | 9/2008 | Olson et al. |
| 2008/0269610 A1 | 10/2008 | Burla et al. |
| 2009/0264760 A1 | 10/2009 | Lazebnik et al. |
| 2010/0121189 A1 | 5/2010 | Ma et al. |
| 2010/0121190 A1 | 5/2010 | Pagoulatos et al. |
| 2010/0160783 A1 | 6/2010 | Halmann et al. |

OTHER PUBLICATIONS

Carr, Jonathan, "Surface Reconstructing in 3D Medical Imaging", Department of Electrical Engineering, University of Canterbury, Christchurch, New Zealand, Feb. 1996, 213 pgs.

First Office Action, Chinese Patent Application 200810006980.0, mailed by the State Intellectual Property Office of People's Republic of China on Jun. 29, 2011, 14 pages.

International Search Report and the Written Opinion issued for PCT/US2009/062976, dated Jan. 7, 2010, 11 pages.

International Search Report and Written Opinion issued for PCT/US2008/075367 dated Nov. 14, 2008, 9 pages.

International Search Report and Written Opinion issued for PCT/US2009/062987 dated Mar. 19, 2010, 11 pages.

International Search Report and Written Opinion issued for PCT/US2009/064093 dated Mar. 4, 2010, 7 pages.

International Search Report and Written Opinion issued for PCT/US2010/030058, dated Jul. 9, 2010, 10 pages.

Office Action dated Mar. 19, 2010 in U.S. Appl. No. 11/749,319, 7 pages.

Office Action dated Oct. 7, 2010 in U.S. Appl. No. 11/749,319, 9 pages.

Office Action issued Jun. 10, 2011 in U.S. Appl. No. 11/749,319, 11 pages.

Carr, J., "Surface Reconstructing in 3D Medical Imaging", Department of Electrical Engineering, University of Canterbury, Christchurch, New Zealand, Feb. 1996, 213 pgs.

Merz, E., "Three dimensional Ultrasound in the Evaluation of Fetal Anatomy and Fetal Malformations", Sonoace International, Dec. 31, 1996, pp. 23-36, vol. 13, No. 4.

Merz, E., et al., Internet Excerpt from "Volume Scanning in the Evaluation of Fetal Malformations: A New Dimension in Prenatal Diagnosis", Journal of Ultrasound in Obstetrics and Gynecology, 1995, pp. 222-227, vol. 5 (Excerpt only 3 pgs.).

Von Ramm et al., "Beam Steering with Linear Arrays," Aug. 1983, IEEE Transactions on Biomedical Engineering, pp. 438-452, vol. BME-30, No. 8.

\* cited by examiner

SYSTEM AND METHOD FOR OPTIMIZED SPATIO-TEMPORAL SAMPLING

CROSS-REFERENCE TO RELATED APPLICATIONS

This application claims priority to U.S. Provisional Patent Application No. 60/886,877 filed Jan. 26, 2007, entitled SYSTEM AND METHOD FOR TEMPORAL COHERENCE SPATIAL SAMPLING, the disclosure of which is hereby incorporated by reference in its entirety.

TECHNICAL FIELD

This disclosure relates to ultrasound imaging and more specifically to systems and methods for optimized spatio-temporal sampling.

BACKGROUND OF THE INVENTION

Spatial compounding is a method of creating an ultrasound image by compiling multiple views or angles. Each view is obtained from multiple lines of sight at different angles. This is a departure from traditional ultrasound imaging that used a single line of sight. The views from the multiple angles are combined to create a single image, thereby reinforcing real-tissue information and suppressing random artifacts. Spatial compounding has resulted in a reduction in speckle noise artifacts; shadowing artifacts and image-degrading artifacts. In addition, such compounding, which is also known as compound imaging, results in improvements in: contrast resolution; needle visualization; tissue contrast resolution; fine-structure delineation; interface/border continuity and lateral edge detection.

The original literature called this technique Compound Imaging. Many companies are now using this technique, calling it various names including: SonoCT; CrossBeam Imaging; and Spatial Compounding.

Some systems use a method where information from both the transmit and the receive beam steering is processed to produce images from multiple view angles. The multiple images are aligned and combined to form an image. Images that are created using both transmit and receive information are typically superior to images consisting of receive information only.

One drawback of the compounding methods now employed is that they result in temporal artifacts being introduced into the final image which, in turn, causes ambiguity to the user.

BRIEF SUMMARY OF THE INVENTION

The present invention is directed to a system and method for spatial compounding on an ultrasound platform to achieve optimized spatio-temporal sampling. This is accomplished by a system and method for mixing the order of steered and straight rays fired within a frame. In one embodiment this is accomplished by changing the firing sequence so that the target region is sampled in subsequent lines as opposed to subsequent frames. Using this approach it is possible to minimize the temporal image artifacts caused by the compounding process. This effectively changes the ray firing sequence to move the location of minimal temporal difference to the desired target point.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1A:
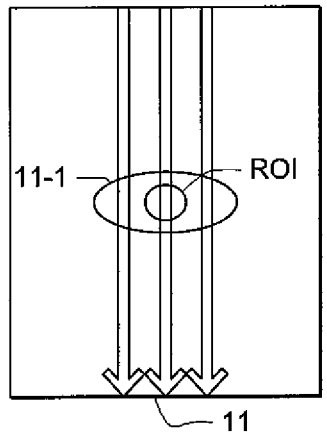
FIGS. 1A through 1D show examples of prior art frame interleaved and ray-interleaved spatial compounding.
Figure 1B:
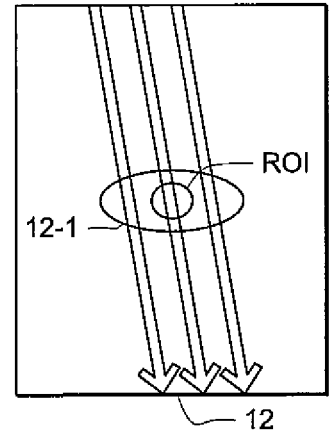
Figure 1C:
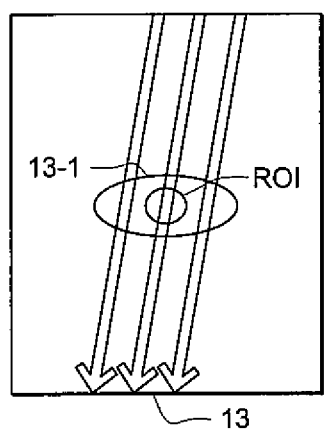

FIGS. 1A through 1C show examples of prior art frame interleaved spatial compounding. In FIG. 1A the beam rays are steered straight, while in FIGS. 1B and 1C the beam rays are steered left and right, respectively. This demonstrates the most common spatial compounding ray firing sequence which consists of acquiring separate frames for each steer direction. For example, frame 11 shows a full frame (only three rays of which are actually drawn) of straight rays 11-1 followed by full frame 12 of steered left rays 12-1 then by a full frame 13 of steered right rays 13-1. These three frames are then compounded together to form a final image. This compounding is difficult because the target may have moved between frames and thus the target will appear different for subsequent frames. In order to achieve the best image it is important to make sure that the different frames are aligned to each other before combining. In some cases extra post-processing is done to modify the frames before combining to minimize temporal artifacts. In this "frame interleaved" approach the least temporal difference for a pixel is on the order of two times the time to acquire a frame (~40 ms for a 128 line 6 cm frame). In the example just discussed, each frame has 128 rays and thus the combination of the three angles (straight, left, right) yields a combination of 384 rays stemming from an ultrasound scan head and passing through a region of interest (ROI).

As discussed above, the time between the collection of the data for all "looks" (straight, left, right) in a region of interest ROI is equal to the time to collect two frames plus the time of flight to the ROI. This time difference then can give rise to motion artifacts in the resulting image.

Figure 1D:
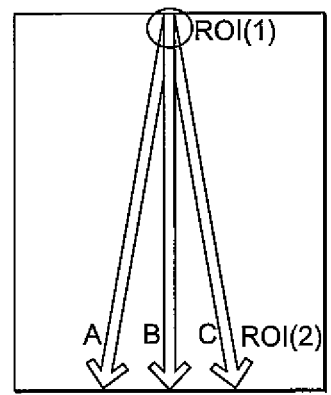

FIG. 1D shows an example of prior art ray interleaved spatial compounding where data from all "looks" is collected in a single frame sequence. For example, for a 128 line frame, rays are fired in sequence A, B, C (A=steer left, B=steer straight, C=steer right), for each ray origin from line 1 to line 128. In this example, there are a total of 384 rays fired. Once the frame containing all look angles is collected, the data are compounded (combined) into a single frame of data. When using this method the time between the collection of the data for all looks in a region of interest (ROI) is dependent on the location of the ROI. For example, the time to collect the data in ROI(1) (near the skin line) is close to the time of flight for two rays, but the time at ROI(2) is much longer, approaching that of the frame interleaved method.

Figure 2A:
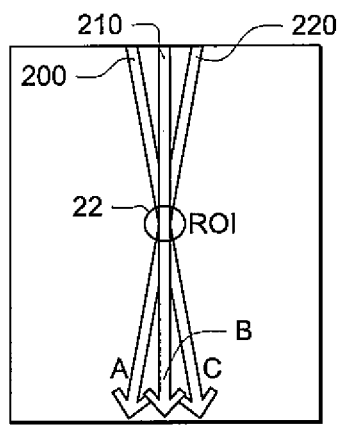
FIGS. 2A through 2C show embodiments of ray interleaved spatial compounding according to the inventive concepts taught herein.
Figure 2B:
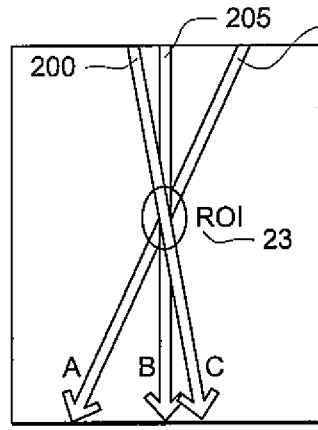
Figure 2C:
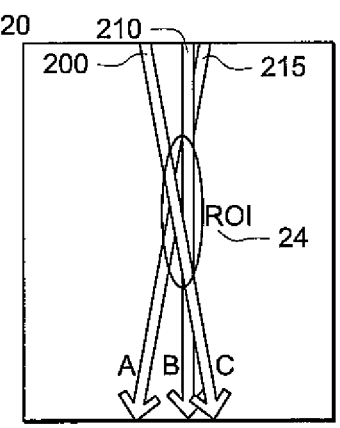

FIGS. 2A through 2C show embodiments of ray interleaved spatial compounding according to the inventive concepts taught herein. FIG. 2A shows one embodiment of ray interleaved spatial compounding with optimized temporal spatial sampling. In this embodiment, data is collected for all "look" angles in one frame sequence, with the ray firing sequence and origins (ordinate location of the beam as it leaves the scan head) being optimized so that the time between subsequent samples from different look angles is minimized in a desired region of interest, such as ROI 22. For example, for a 128 line frame, rays are fired in sequence A, B, C (A=steer left, B=steer straight, C=steer right), but the ray origins are modified by the time difference of the starting point as reflected by the numbers 200, 210 and 220 which correspond to origin positions so that the temporal difference is minimized in the ROI. In this example there are a total of 384 rays fired. Once the frame containing all look angles is collected, the date are compounded (combined) into a single frame of data. When using this method, the time to collect the data in the ROI is close to the time of flight for two rays plus the time of flight to ROI 22. This method minimizes motion artifacts in the ROI region.

FIG. 2B is a variation of FIG. 2A illustrating how the ray origin (shown by ray B originating from point 205 instead of from point 210 (as shown in FIG. 2A) can be modified to optimize the temporal sampling at ROI 23 with rays of asymmetric angles.

FIG. 2C shows one embodiment of ray interleaved spatial compounding with optimized temporal spatial sampling for an expanded ROI, such as ROI 24, using asymmetric spacing of the rays. It is possible, by varying either the position along the scan head a ray is fired from and/or the angle of the fired ray, to modify the ROI. The changing of the ROI then can be used in some procedures, for example, when tracking the insertion through a body of a needle, the ROI can be changed to coincide with the movement of the needle or other medical probe. In this manner the caregiver can keep the end (or other portion) of the probe in "view". Also, by focusing on multiple ROI's, such as on the probe tip and the target, the trajectory of the probe is precisely adjustable.

As shown in FIGS. 2A, 2B and 2C, the order of steered and straight (steered straight) rays fired within a frame can be mixed so as to create the desired spatial sample. An example of a frame of this type would be made up of loops such as the following:

1) A loop of steered left rays;
2) A loop of steered left rays and steered straight rays;
3) A loop of steered left rays, steered right rays and steered straight rays;
4) A loop of steered right rays and steered straight rays;
5) A loop of steered right rays.

The length of loops 1, 2, 4 and 5 are defined, in one embodiment, by equation (1):

$$\text{Loop Length} = \text{round}(\tan(\text{steer angle})*\text{screen depth}/2)/\text{pitch})*\text{line density} \quad 1)$$

The length of loop 3 is defined, in one embodiment, by equation (2):

$$\text{Inner Loop Length} = (\text{Total elements}*\text{line density}) - 2*\text{Loop Length} \quad 2)$$

One particular use for an improved image created by the above-described method is for anesthesia applications as well as for other high quality, artifact free, imaging applications where precise imaging is of prime importance.

As shown in FIG. 2A, rays 200, 210 and 220 (numbered to reflect origin positions) are fired in sequence and steered such that they are least temporally different in the target region, such as region 22. Region 22 can be a point or a region of interest depending on the relative steerage angles of rays 200, 210 and 220 as discussed above. While in the embodiments shown only three rays are shown forming a convergence, any number of rays, including all of the rays in the frame, can be used to define the optimized temporal difference range. In one embodiment, the angle of the steered rays can be adjusted and in other embodiments the sequence of ray origins (or a combination of sequence and angle) can be adjusted.

Figure 3A:
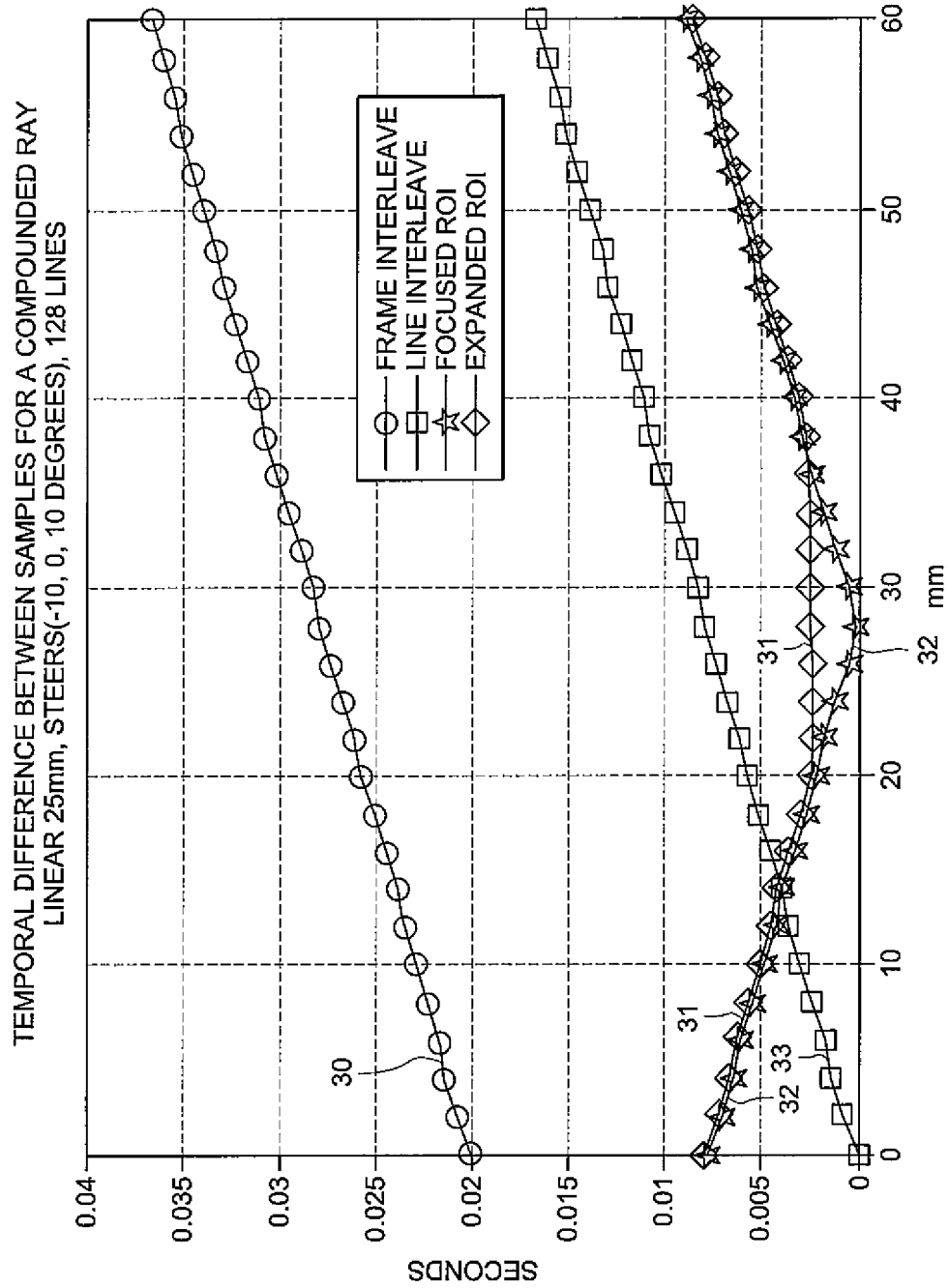
FIGS. 3A and 3B are charts showing ray temporal differences between samples for a compounded ray.
Figure 3B:
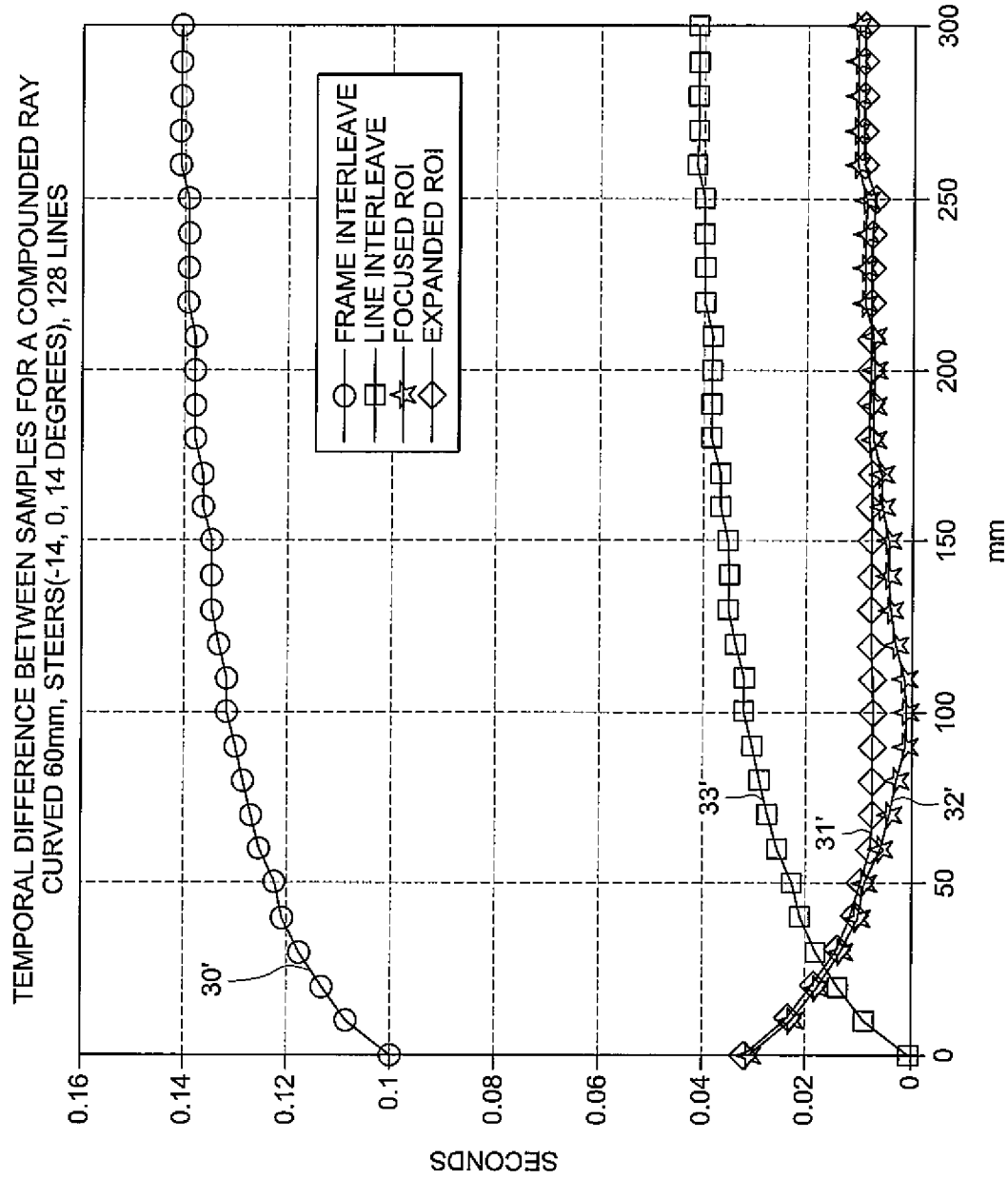

FIGS. 3A and 3B are charts showing ray temporal differences between samples for a compounded ray. As shown in FIG. 3A, line 30 represents linear frame interleaving with steers of −10, 0 and +10 degrees. Line 33 represents line interleaving. Line 32 shows the results of a focused ROI while line 31 shows the results for an expanded ROI.

FIG. 3B shows line 30' representing curved frame interleaving with steers of −14, 0 and +14 degrees. Line 33' represents line interleaving. Line 32' shows the results of a focused ROI while line 31' shows the results for an expanded ROI.

Figure 4:
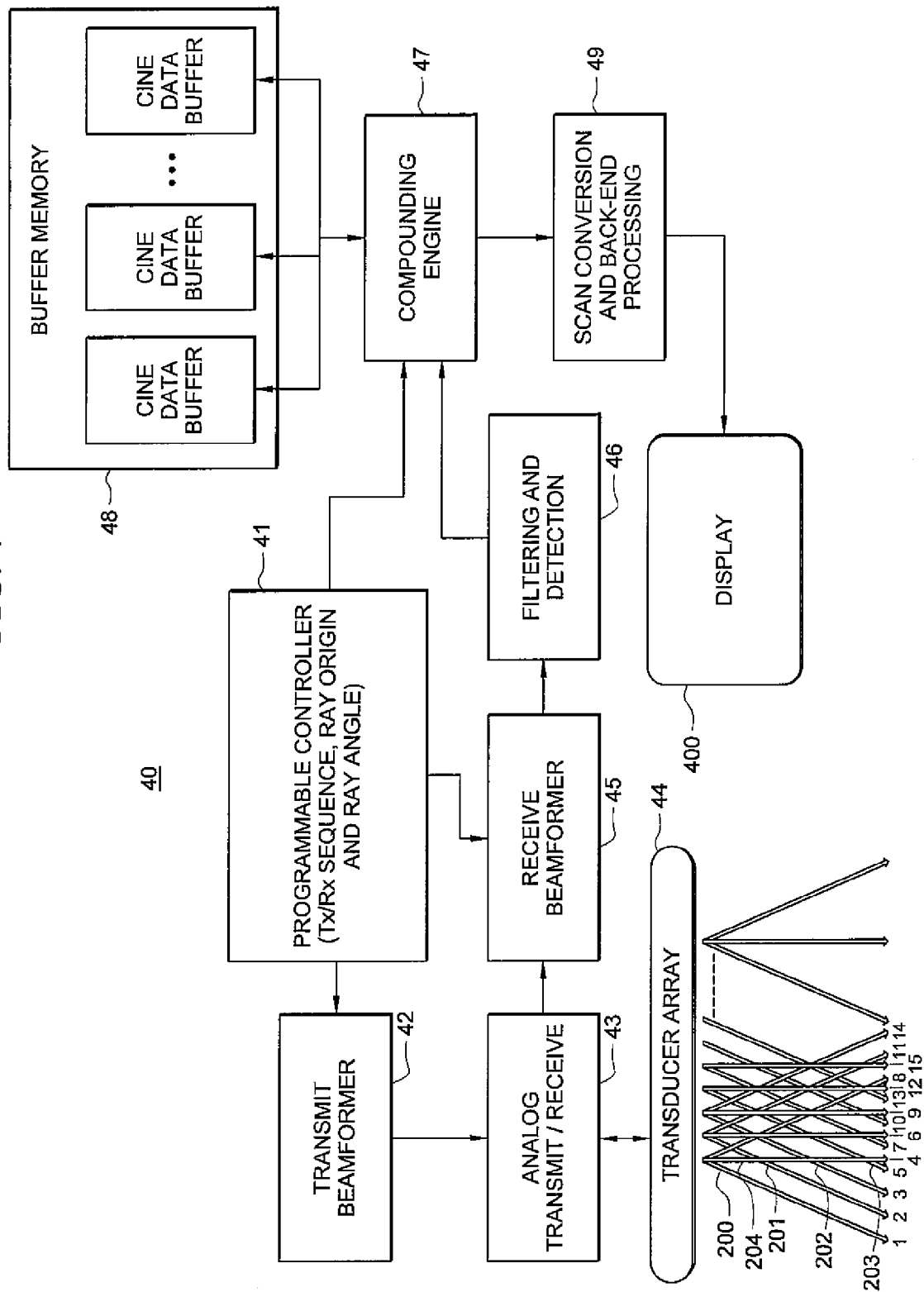
FIG. 4 shows one embodiment of an implementation of the concepts discussed herein.

FIG. 4 shows one embodiment 40 of an implementation of the concepts discussed herein. Controller 41 generates the transmit sequence as well as the steerage angle for the beams in conjunction with beamformer 42 and analog transmitter 43. Controller 41 can comprise, for example, one or more processors that perform the ray angle adjustment or the ordinate location control for the respective rays of each time frame. The output of transmitter 43 supplies the transmit signals to transducer array 44. The output from transducer 44 is a sequence of rays which are used for image forming by "bouncing" back from a target within a subject.

In the example, there are 128 rays for each steer angle (the rays are numbered in an example firing sequence using three steers) in each time differentiated frame. The returned signal for each fired ray is received by array 44 and communicated via analog receiver 43 to receive beamformer 45. The output of the receive beamformer is a digitally sampled and beamformed ray. This ray is then filtered and detected by controller 46 and sent to compounding engine 47 for compounding in association with the transmitted signals. Each collection of similarly steered rays are aligned, scan converted into a common grid and buffered by the compounding engine and stored in buffer memory 48. When enough data is present to compound (or combine) the data from different steers, the compounding engine computes a weighted average for each common sample in the buffer memory for the given frame of ultrasound data. The compounded data is then sent from the compounding engine to the scan converter 49 for processing for display 400.

The system and method discussed herein can be extended to many scan head types, such as, for example, phased and curved types, even though it was developed on a linear scan head. The procedures used herein can be focused on a "region of interest," one of which is the middle of the screen. Also note that the looping example is one implementation and other loop orders can be used as well as reverse order loops and the addition of additional loops to cover additional steer directions. Note also that in the context of the discussion herein steered straight need not be perfectly straight but could have some distortion thereto in the order of, say, five degrees. Also, the ray called "straight" need not be used if desired.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of forming an ultrasound image based upon image forming rays transmitted into a subject, said method comprising:

mixing an order of said rays fired within a beam frame, said mixing comprising:

adjusting a ray firing sequence of particular rays to move a location of optimized temporal difference between different rays of a common frame to a desired region of interest in said subject;

asymmetrically spacing said frame's rays so that paths of said frame's rays intersect at a plurality of points having different depths within said subject to provide a region of interest encompassing said different depths; and wherein said frame comprises at least one loop having a loop length defined by equation: loop length=round (tan(steer angle)*screen depth/2)/pitch)*line density and wherein at least one other loop has a loop length defined by equation: loop length=(total elements*line density)−2*loop length.

2. A method of forming an ultrasound image based upon image forming rays transmitted into a subject, said method comprising:

mixing an order of said rays fired within a beam frame, said mixing comprising:

adjusting a ray firing sequence of particular rays to move a location of optimized temporal difference between different rays of a common frame to a desired region of interest in said subject;

asymmetrically spacing said frame's rays so that paths of said frame's rays intersect at a plurality of points having different depths within said subject to provide a region of interest encompassing said different depths; and wherein said frame comprises:

loop 1, which is a loop of steered left rays;

loop 2, which is a loop of steered left rays and steered straight rays;

loop 3, which is a loop of steered left rays, steered right rays and steered straight rays;

loop 4, which is a loop of steered right rays and steered straight rays;

loop 5, which is a loop of steered right rays, wherein a length of loops 1, 2, 4 and 5 are defined, by equation: loop length=round(tan(steer angle)*screen depth/2)/pitch*line density and wherein the length of loop 3 is defined by equation: loop length=(total elements*line density)−2*loop length.

* * * * *